(12) United States Patent
Lee et al.

(10) Patent No.: US 6,790,979 B2
(45) Date of Patent: Sep. 14, 2004

(54) CURCUMIN ANALOGUES AND USES THEREOF

(75) Inventors: Kuo-Hsiung Lee, Chapel Hill, NC (US); Junko Ishida, Tokyo (JP); Hironari Ohtsu, Chapel Hill, NC (US); Hui-Kang Wang, Chapel Hill, NC (US); Hideji Itokawa, Chapel Hill, NC (US); Chawnshang Chang, Pittsford, NY (US); Charles C-Y. Shih, Solana Beach, CA (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/124,642

(22) Filed: Apr. 17, 2002

(65) Prior Publication Data

US 2003/0203933 A1 Oct. 30, 2003

(51) Int. Cl.$^7$ ................................................ C07C 69/76
(52) U.S. Cl. .................... 560/53; 568/325; 514/541; 514/646
(58) Field of Search ........................... 560/53; 568/325; 514/544, 646

(56) References Cited

FOREIGN PATENT DOCUMENTS

| WO | WO 01/30335 | 5/2001 |
|---|---|---|
| WO | WO 01/40188 | 6/2001 |

OTHER PUBLICATIONS

McDonald, R et al, Anti–Cancer Drug Design (2001), 16(6) 261–270.*
Parveen, I., et al., *Labeled Compounds of Interest as Antitumor Agents*, Chem. Abstract., vol. 133, No. 281645 (2000).
Martono, S., *Inhibitory Effects of Curcumin and its Analogs on In Vitro Rat Liver Glutathione S–Transferases Activity*, Chem. Abstract., vol. 128, No. 110377 (1996).
Gorbitz, C.H. et al., *Structural Studies of Curcuminoids, V. Crystal Structures of 1,7,–bis (3,4–dimethoxyphenyl)–4–benzyl–1, 6–heptadiene–3, 5–dione*, Chem. Abstract., vol. 107, No. 6988 (1986).
Pedersen et al., *Synthesis of Naturally Occuring Curcuminoids and Related Compounds*; Chem. Abstract., vol. 103, No. 178092 (1985).
Choshi et al., *Synthesis of Dibenzoylmethane Derivatives and Inhibition of Mutagenicity in Salmonella Typhimurium*, Chem. Abstract., vol. 117, No. 48036 (1992).
McDonald et al., *Synthesis and Anticancer Activity of nordihydrogualaretic Acid and Analogues*, Chem. Abstract., vol. 138, No. 362138 (2001).
Artiser, Jack L., et al., *Curcumin Is an In Vivo Inhibitor of Angiogenesis*, Molecular Medicine, vol. 4, pp. 376–383 (1998).
Ishida, Junko, et al., *Antitumor–promoting effects of cyclic diarylheptanoids on Epstein–Barr virus activation and two–stage mouse skin carcinogenesis*, Cancer Letters, vol. 159, pp. 135–140 (2000).
Nurfina, A. N., et al., *Synthesis of some symmetrical curcumin derivatives and their anti–inflammatory activity*, Eur. J. Med. Chem.., vol. 32, pp. 321–328 (197).
Ruby, A.J., et al., *Anti–tumour and antioxidant activity of natural curcuminoids*, Cancer Letters, vol. 94, pp. 79–83 (1995).
Sugiyama, Yasunori, et al., *Involvement of the β–Diketone Moiety in the Antioxidantive Mechanism of Tetrahydrocurcumin*, Biochemical Pharmacology, vol. 52, pp. 519–525 (1996).
Syu, Wan–Jr, et al., *Cytotoxicity of Curcuminoids and Some Novel Compounds from Curcuma zedoaria*, J. Nat. Prod., vol. 61, pp. 1531–1534 (1998).

* cited by examiner

Primary Examiner—Paul J. Killos
(74) Attorney, Agent, or Firm—Myers Bigel Sibley & Sajovec

(57) ABSTRACT

The present invention relates to compounds capable of acting as androgen receptor antagonists, pharmaceutical formulations containing the same, and methods of use thereof. Such uses include, but are not limited to, use as antitumor agents, particularly for the treatment of cancers such as colon, skin and prostate cancer and to induce androgen receptor antagonist activity in a subject afflicted with an androgen-related affliction. Examples of androgen-related afflictions include, but are not limited to, baldness, hirsutism, behavioral disorders, acne, and uninhibited spermatogenesis wherein inhibition of spermatogenesis is so desired.

33 Claims, 5 Drawing Sheets

| | $R_1$ | $R_2$ | $R_3$ | $R_4$ |
|---|---|---|---|---|
| 1 | OCH$_3$ | OCH$_3$ | H | H |
| 2 | OCH$_3$ | H | H | H |
| 3 | H | H | H | H |
| 4 | OCH$_3$ | OCH$_3$ | CH$_3$ | CH$_3$ |

| | $R_1$ | $R_2$ | $R_3$ | $R_4$ |
|---|---|---|---|---|
| 5 | OCH$_3$ | OCH$_3$ | H | H |
| 6 | OCH$_3$ | H | H | H |
| 7 | H | H | H | H |
| 8 | OCH$_3$ | OCH$_3$ | CH$_3$ | CH$_3$ |

| | $R_1$ | $R_2$ |
|---|---|---|
| 9 | H | H |
| 10 | CH$_3$ | CH$_3$ |

| | $R_6$ | $R_7$ |
|---|---|---|
| 11 | =O | =O |
| 12 | =O | -OH |
| 13 | -OH | -OH |

| | $R_5$ | $R_6$ | $R_7$ |
|---|---|---|---|
| 14 | H | =O | =O |
| 15 | H | =O | -OH |
| 16 | H | -OH | -OH |
| 17 | CH$_3$ | =O | -OH |
| 18 | CH$_3$ | -OH | -OH |

| | $R_1$ | $R_3$ | $R_4$ |
|---|---|---|---|
| 19 | OCH$_3$ | CH$_2$COOCH$_3$ | H |
| 20 | OCH$_3$ | CH$_2$COOCH$_3$ | CH$_2$COOCH$_3$ |

|    | R₁   | R₃ | R₈      |
|----|------|-----|---------|
| 21 | H    | H   | COOH    |
| 22 | OCH₃ | OH  | COOC₂H₅ |
| 23 | OCH₃ | OH  | COOH    |

|    | R₁ | R₂  | R₃   | R₄ |
|----|----|-----|------|----|
| 24 | H  | H   | F    | H  |
| 25 | H  | F   | H    | H  |
| 26 | F  | H   | H    | H  |
| 27 | H  | F   | OMe  | H  |
| 28 | H  | CF₃ | F    | H  |
| 29 | H  | H   | OCF₃ | H  |

|    | R₁  | R₂ | R₃     |
|----|-----|-----|--------|
| 30 | H   | H   | C=O    |
| 31 | H   | H   | C=N-OH |
| 32 | CH₃ | OH  | C=O    |

|    | R₁  | R₂  | R₃   |
|----|-----|-----|------|
| 33 | H   | H   | C=O  |
| 34 | CH₃ | H   | C=O  |
| 35 | CH₃ | CH₃ | C=O  |
| 36 | Ac  | Ac  | C=O  |
| 37 | H   | H   | ⟨O/O⟩ |
| 38 | H   | H   | ⟨S/S⟩ |

|    | R₁   | R₂   | R₃   | R₃'  | R₄     |
|----|------|------|------|------|--------|
| 39 | H    | OCH₃ | OCH₃ | OCH₃ | H      |
| 40 | OCH₃ | H    | OCH₃ | OCH₃ | H      |
| 41 | H    | H    | OCH₃ | NO₂  | Br     |
| 42 | H    | H    | NO₂  | NO₂  | Br     |
| 43 | H    | H    | NO₂  | NO₂  | H      |
| 44 | H    | H    | H    | H    | CH₂CO  |

CURCUMIN ANALOGUES AND USES THEREOF

STATEMENT OF FEDERAL SUPPORT

This invention was made with Government support under Grant No. CA-17625 and Grant No. CA-55639. The government has certain rights in this invention.

FIELD OF THE INVENTION

The present invention relates to compounds capable of acting as androgen receptor antagonists, pharmaceutical formulations containing the same, and methods of use thereof.

BACKGROUND OF THE INVENTION

The androgen receptor (AR) is a member of a large family of ligand-dependent transcriptional factors known as the steroid receptor superfamily. Chang et al., *Proc. Natl. Acad. Sci. USA*, 85, 7211–7215 (1988). Beato, M., *Cell*, 56, 335–344 (1989). Androgens and the AR play an important role in the growth of the normal prostate and prostate cancer. Prostate cancer represents the most common male malignancy in the United States. Landis et al., *Cancer J. Clin.*, 48, 6–29 (1998). Recently, antiandrogens such as hydroxyflutamide (HF) in combination with surgical or medical castration have been widely used for the treatment of prostate cancer. Crawford et al., *New Engl. J. Med.*, 321, 419–424 (1989). Several compounds, including cyprosterone, HF, and bicalutamide (shown below), have been used clinically in the treatment of prostate cancer.

Chart 1
Structures of cyprosterone, hydroxflutamide, and bicalutamide

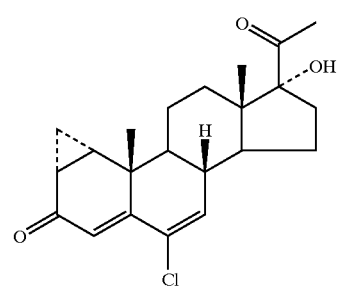

Cyprosterone

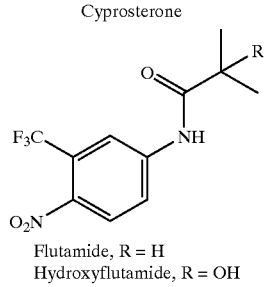

Flutamide, R = H
Hydroxyflutamide, R = OH

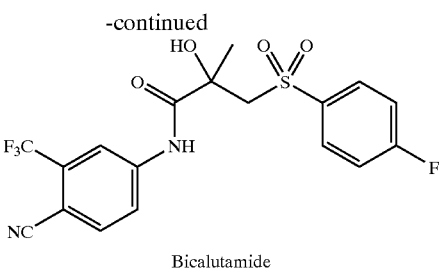

Bicalutamide

The synthetic steroidal antiandrogen cyprosterone is one of the first antiandrogens used clinically in Europe, McLeod, D., G., *Cancer*, 71, 1046–1049 (1993) but it has many side effects. Neumann et al., *J. Clin. Oncol.*, 1, 41–65 (1982). HF and bicalutamide are both nonsteroidal antiandrogens. Bicalutamide is a newer nonsteroidal antiandrogen originally thought to have a pure antiandrogen activity without agonist activity. It has a longer half-life (6 days) and a higher binding affinity to the AR than HF. Verhelst et al., *Clin. Endocrinol.*, 41, 525–530 (1994). (a) Kelly et al., *J. Urol.* (1993), 149, 607–609; (b) Scher et al., Prostate Cancer. *J. Clin. Oncol.*, 11, 1566–1572 (1993).

Although antiandrogen hormone therapy has been widely used for the treatment for prostate cancer, some antiandrogens may act as AR agonists which may result in "antiandrogen withdrawal syndrome." Miyamoto et al., *Proc. Natl. Acad. Sci. USA*, 95, 7379–7384 (1998). A currently accepted hypothesis postulates that mutations in androgen receptors may account for why HF, the active metabolite of flutamide, can activate androgen receptor target genes and stimulate prostate cancer growth. Miyamoto et al., *Proc. Natl. Acad. Sci. USA*, 95, 7379–7384 (1998). The same mechanism is used to explain the "flutamide withdrawal syndrome," in which patients who experience an increase in prostate-specific antigen (PSA) while taking flutamide, have a decrease in PSA after withdrawal of treatment. Indeed, HF can activate androgen receptor target genes, such as PSA and MMTV-LTR (a reporter gene which expressed androgen-response element), in the presence of ARA70, the first identified androgen receptor co-activator. Yeh et al., *The Lancet*, 349, 852–853 (1997). Because this syndrome often leads to the failure of androgen-ablative therapy, it is desirable to develop better antiandrogens without agonist activity.

The phenolic diarylheptanoid curcumin (1) is the major pigment in turmeric. Curcumin and its analogs show potent anti-oxidant activity, anti-inflammatory activity, Nurfina et al., *Eur. J. Med. Chem.*, 32, 321–328 (1997) cytotoxicity against tumor cells, Syu et al., *J. Nat. Prod.*, 61, 1531–1534 (1998), antitumor-promoting activities, Sugiyama et al., *Biochem. Pharmacol.*, 52, 519–525 (1996). Ruby et al., *Cancer Lett.*, 94, 79–83 (1995) and antiangiogenesis activity (J. L. Arbiser et al. *Mol. Med.* 4: 376 (1998)).

Two cyclic diarylheptanoids, 13-oxomyricanol and myricanone, exhibiting potent antitumor promoting effects on DMBA-initiated and TPA-induced mouse skin carcinogenesis have been reported. Ishida et al., *Cancer Lett.*, 159. 135–140 (2000). In the present study, a number of novel curcumin analogues have been prepared and evaluated for antagonistic activity against the AR in the presence of androgen receptor coactivator, ARA70, using two human prostate cancer cell lines, PC-3 and DU-145. PC-3 cells are androgen-independent tumor cells that do not express functional AR. DU-145 cells are androgen-independent tumor cells that also do not express functional AR.

SUMMARY OF THE INVENTION

According to embodiments of the present invention, the present invention relates to a compound according to formula I:

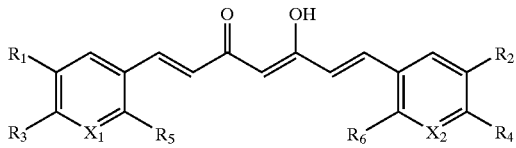

(I)

wherein:
$R_1$ and $R_2$ are each independently selected from the group consisting of alkoxy, nitro, amino, and dialkylamino;
$R_3$ and $R_4$ are each independently selected from the group consisting of hydroxy, alkoxy, and —$OR_7C(O)R_8$, wherein $R_7$ is lower alkylene and $R_8$ is alkoxy;
or $R_1$ and $R_3$ together are alkylenedioxy;
or $R_2$ and $R_4$ together are alkylenedioxy;
$R_5$ and $R_6$ are each independently selected from the group consisting of H, halogen, and nitro;
$X_1$ is N, or $X_1$ is C bonded to a H, alkoxy or nitro; and
$X_2$ is N, or $X_2$ is C bonded to a H, alkoxy or nitro.

According to still other embodiments of the present invention, the present invention relates to a compound according to formula II:

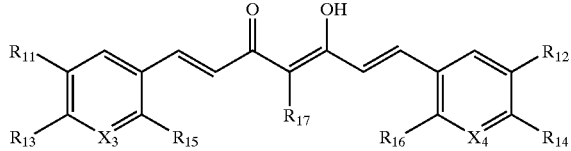

(II)

wherein:
$R_{11}$ and $R_{12}$ are each independently selected from the group consisting of alkoxy, nitro, amino, and dialkylamino;
$R_{13}$ and $R_{14}$ are each independently selected from the group consisting of hydroxy, alkoxy, and —$OR_{18}C(O)R_{19}$, wherein $R_{18}$ is lower alkylene and $R_{19}$ is alkoxy.
or $R_{11}$ and $R_{13}$ together are alkylenedioxy;
or $R_{12}$ and $R_{14}$ together are alkylenedioxy;
$R_{15}$ and $R_{16}$ are each independently selected from the group consisting of H, halogen, and nitro;
$R_{17}$ is —$R_{20}C(O)OR_{21}$, wherein $R_{20}$ is alkylene and $R_{21}$ is H or alkyl;
$X_3$ is N, or $X_3$ is C bonded to a H, alkoxy or nitro; and
$X_4$ is N, or $X_4$ is C bonded to a H, alkoxy or nitro.

According to yet other embodiments of the present invention, the present invention relates to compounds according to the formula III:

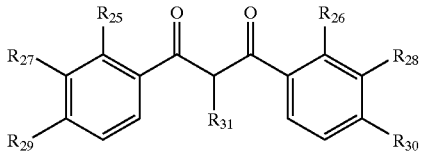

(III)

wherein:
$R_{25}$ and $R_{26}$ are each independently H or lower alkyl;
$R_{27}$, $R_{28}$, $R_{29}$ and $R_{30}$ are each alkoxy;
$R_{31}$ is H or lower alkyl.

According to still other embodiments of the present invention, the present invention relates to a method of treating cancer, comprising administering to a subject in need thereof a treatment effective amount of a compound according to the formulas above. Examples of cancers that may be treated include, but are not limited to, skin cancer, small cell lung cancer, testicular cancer, lymphoma, leukemia, esophageal cancer, stomach cancer, colon cancer, breast cancer, endometrial cancer, ovarian cancer, central nervous system cancer, liver cancer and prostate cancer.

According to yet other embodiments of the present invention, the present invention relates to a method of inducing androgen receptor antagonist activity, the method comprising contacting a cancer cell with an androgen receptor antagonist effective amount of a compound according to the formulas above.

According to other embodiments of the present invention, the present invention relates to a method of inducing androgen receptor antagonist activity in a subject afflicted with an androgen-related affliction. Examples of androgen-related afflictions include, but are not limited to, baldness, hirsutism, behavioral disorders, acne, and uninhibited spermatogenesis wherein inhibition of spermatogenesis is so desired.

DETAILED DESCRIPTION OF THE INVENTION

Figure 1:
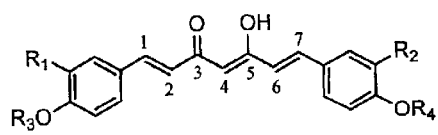
FIG. 1 illustrates structures of curcumin analogues (1–20)
Figure 1:
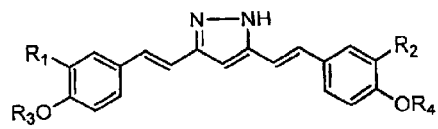
Figure 1:
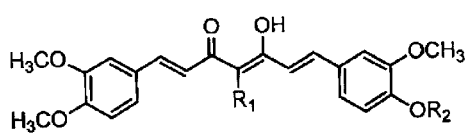
Figure 1:
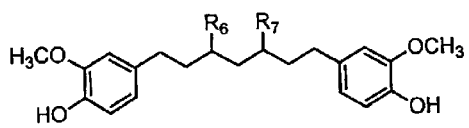
Figure 1:
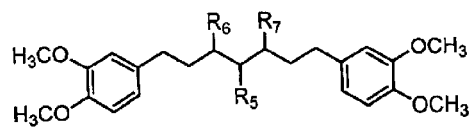
Figure 1:
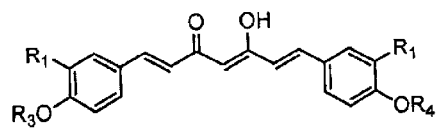

The present invention will now be described more fully hereinafter with reference to the accompanying figures, which further illustrate the invention described herein. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

The term "alkyl" or "loweralkyl" as used herein refers to C1 to C4, C6 or C8 alkyl, which may be linear or branched and saturated or unsaturated.

"Cycloalkyl" is specified as such herein, and is typically C3, C4 or C5 to C6 or C8 cycloalkyl.

"Alkenyl" or "loweralkenyl" as used herein likewise refers to C1 to C4 alkenyl, and alkoxy or loweralkoxy as used herein likewise refers to C1 to C4 alkoxy.

"Alkoxy" as used herein refers to linear or branched, saturated or unsaturated oxo-hydrocarbon chains, including for example methoxy, ethoxy, propoxy, isopropoxy, butoxy, and t-butoxy.

The term "aryl" as used herein refers to C3 to C 10 cyclic aromatic groups such as phenyl, naphthyl, and the like, and includes substituted aryl groups such as tolyl. "Halo" as used herein refers to any halogen group, such as chloro, fluoro, bromo, or iodo.

The term "hydroxyalkyl" as used herein refers to C1 to C4 linear or branched hydroxy-substituted alkyl, i.e., —CH$_2$OH, —(CH$_2$)$_2$OH, etc.

The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc.

The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

The term "alkylenedioxy" refers to a group of the general formula —OR'O—, —OR'OR'—, or —R'OR'OR'— where each R' is independently alkyl.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

"Androgen" as used herein refers to sex hormones generally known to those skilled in the art and include, but are not limited to, testosterone, dihydrotestosterone, and androstenedione and compounds known to act in mechanisms similar to androgens such as androgen receptor agonists. "Androgen" relates to a hormone or compound, or a combination thereof.

"Antiandrogen withdrawal syndrome" as used herein refers to a phenomenon characterized by either no change or an increase in serum prostate-specific antigen (PSA) concentration upon administration of antiandrogen therapy, and a subsequent decreased PSA concentration observed after withdrawal of antiandrogen therapy.

"Androgen receptor antagonist" as used herein refers to a compound that partially or completely inhibits the activity of an androgen receptor agonist.

"Androgen-related affliction" as used herein refers to conditions wherein an androgen or combination of androgens play a role in the condition observed.

The present invention is concerned primarily with the treatment of human subjects, but may also be employed for the treatment of other animal subjects (i.e., mammals, avians) for veterinary purposes. Mammals are preferred, with humans being particularly preferred.

In general, active compounds of the present invention comprise a structure according to the following formulas:

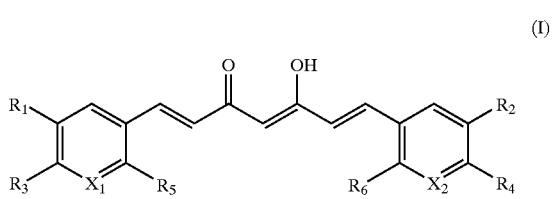

(I)

wherein:
$R_1$ and $R_2$ are each independently selected from the group consisting of alkoxy, nitro, amino, and dialkylamino;
$R_3$ and $R_4$ are each independently selected from the group consisting of hydroxy, alkoxy, and —OR$_7$C(O)R$_8$, wherein $R_7$ is lower alkylene and $R_8$ is alkoxy;
or $R_1$ and $R_3$ together are alkylenedioxy;
or $R_2$ and $R_4$ together are alkylenedioxy;
$R_5$ and $R_6$ are each independently selected from the group consisting of H, halogen, and nitro;
$X_1$ is N, or $X_1$ is C bonded to a H, alkoxy or nitro; and
$X_2$ is N, or $X_2$ is C bonded to a H, alkoxy or nitro;

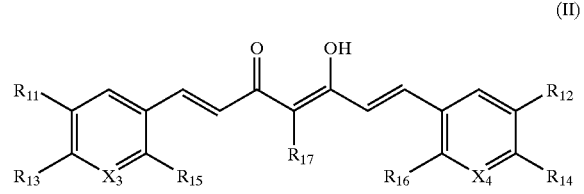

(II)

wherein:
$R_{11}$ and $R_{12}$ are each independently selected from the group consisting of alkoxy, nitro, amino, and dialkylamino;
$R_{13}$ and $R_{14}$ are each independently selected from the group consisting of hydroxy, alkoxy, and —OR$_{18}$C(O)R$_{19}$, wherein $R_{18}$ is lower alkylene and $R_{19}$ is alkoxy.
or $R_{11}$ and $R_{13}$ together are alkylenedioxy;
or $R_{12}$ and $R_{14}$ together are alkylenedioxy;
$R_{15}$ and $R_{16}$ are each independently selected from the group consisting of H, halogen, and nitro;
$R_{17}$ is —R$_{20}$C(O)OR$_{21}$, wherein $R_{20}$ is alkylene and $R_{21}$ is H or alkyl;

$X_3$ is N, or $X_3$ is C bonded to a H, alkoxy or nitro; and
$X_4$ is N, or $X_4$ is C bonded to a H, alkoxy or nitro; and

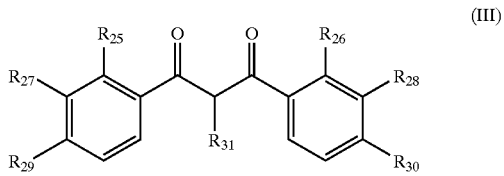

(III)

wherein:

$R_{25}$ and $R_{26}$ are each independently H or lower alkyl;
$R_{27}$, $R_{28}$, $R_{29}$ and $R_{30}$ are each alkoxy;
$R_{31}$ is H or lower alkyl.

A. Specific Compounds

Specific compounds within the scope of the present invention include, but are not limited to:

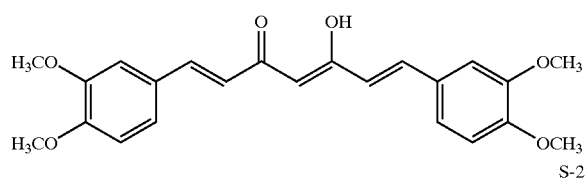

S-1

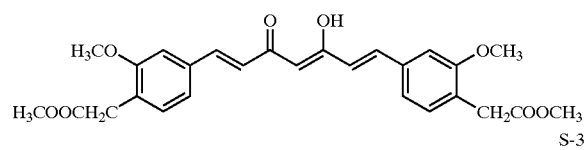

S-2

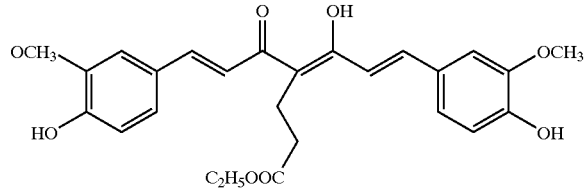

S-3

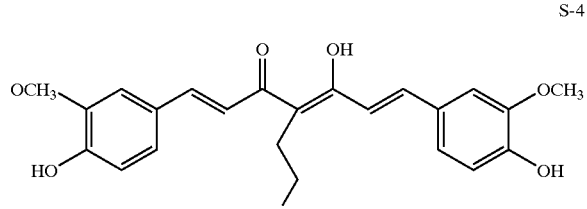

S-4

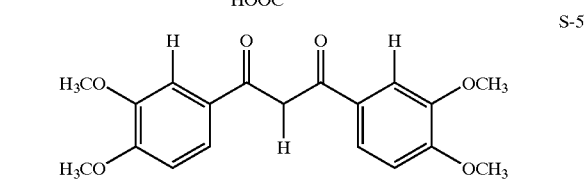

S-5

B. Synthesis of Compounds

Variations on the following general synthetic methods will be readily apparent to those skilled in the art and are deemed to be within the scope of the present invention.

Figure 2:
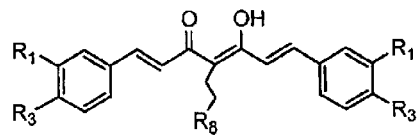
FIG. 2 illustrates structures if curcumin analogues (21–44)
Figure 2:
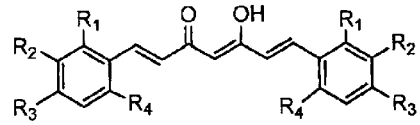
Figure 2:
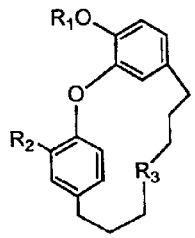
Figure 2:
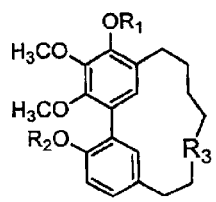
Figure 2:
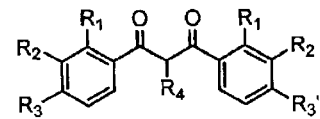

FIGS. 1 and 2 show the structures of curcumin analogues and 1,3-diaryl-1,3-diketopropane derivatives. Curcumin (1), demethoxycurcumin (2) and bisdemethoxycurcumin (3) were obtained by column chromatography (silica gel, $CHCl_3$-MeOH) of commercially available curcumin (Aldrich), which contained 2 and 3 as minor components. Treatment of 1 with diazomethane gave dimethylated curcumin (4) and monomethylated curcumin (9). Methylation of 1 with methyl iodide and $K_2CO_3$ furnished the trimethylated derivative 10, in which a methyl group was also introduced at the C-4 position. Compounds 5–8 were synthesized by heating 1–4 with histidine hydrazide, AcOH and p-TsOH overnight. Hydrogenation of 1 with 10% Pd—C gave a mixture of 11–13. Similarly, compounds 14–16 and 17–18 were obtained by hydrogenation of 4, and 10, respectively. Heating 1 with methyl chloroacetate, NaI and $K_2CO_3$ in acetone furnished a mixture of monomethoxycarbonylmethyl ether 18 and bis-methoxycarbonylmethyl ether 19, which were separated by preparative TLC (PLC). Compounds 21–23 were prepared from benzene or vanillin and ethyl 4-acetyl-5-oxohexanoate by a method known in the art. Pedersen et al., *Liebigs Ann. Chem.*, 1557–1569 (1985). Compounds 21–23 constitute an unseparable mixture of keto-enol tautomeric isomers. The syntheses of 24–38 were described in our previous paper. Ishida et al., *Cancer Lett.*, 159. 135–140 (2000). Ishida et al., Synthesis and Evaluation of Curcumin Analogues as Cytotoxic Agents. Unpublished data. Compounds 3944 were purchased from Aldrich, Inc (Milwaukee, Wis.).

C. Pharmaceutically Acceptable Salts

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

D. Pharmaceutical Formulations

The curcumin analogues of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

E. Methods of Use

In addition to the compounds of the formulas described herein, the present invention also provides useful therapeutic methods. For example, the present invention provides a method of inducing cytotoxicity against tumor cells, antitumor-promoting activities, anti-inflammatory activity. More specifically, the present invention provides a method of inducing androgen receptor antagonist activity. The androgen receptor antagonist activity is a useful means of inhibiting androgen related tumor or cancer cell growth.

Cancer cells which may be inhibited include cells from skin cancer, small cell lung cancer, testicular cancer, lymphoma, leukemia, esophageal cancer, stomach cancer, colon cancer, breast cancer, endometrial cancer, ovarian cancer, central nervous system cancer, liver cancer and prostate cancer.

The present invention also provides a method of treating cancer in a subject afflicted with cancer. These subjects also include subjects afflicted with antiandrogen withdrawal syndrome. The method includes administering to the subject in an effective cancer-treating amount a compound of the formulas of the present invention. The method is useful for the treatment of a variety of cancer cells which include but are not limited to skin cancer, small cell lung cancer, testicular cancer, lymphoma, leukemia, esophageal cancer, stomach cancer, colon cancer, breast cancer, ovarian cancer, central nervous system cancer, liver cancer and prostate cancer.

Compounds with anti-androgen activity also have the potential to be therapeutically useful for treatment of androgen-potentiated hair disorders such as baldness and hirsutism. Anti-androgenic compounds may also be therapeutically useful as a form of male contraception where it is generally known and understood by those skilled in the art that androgens are required to maintain spermatogenesis. Additionally, compounds with anti-androgenic activity may be useful for the treatment of behavioral disorders which include, but are not limited to, aggressiveness, violent behavior and sexual aggression. Anti-androgenic compounds may also be therapeutically useful for the treatment of acne due to the altered levels of hormones, including androgens, associated with acne disorders.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of formulae described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLES

A. Materials and Methods

Compounds 1–3 were obtained by column chromatography (silica gel, $CHCl_3$-MeOH) of commercially available curcumin (Aldrich), which contained 2 and 3 as minor components. Compounds 39–44 were purchased from Aldrich, Inc (Milwaukee, Wis.).

Dimethylcurcumin (4). Curcumin (1) in $Et_2O$ and MeOH was treated with excess of diazomethane in ether for 24 h. The solvents were removed in vacuo and the residue was purified by silica gel column chromatography and PLC to yield yellow needles of 4 (yield 19.8%); mp 129–130° C. (MeOH) (Roughley et al., *J. Chem. Soc. Perkin I,* 2379–2388 (1973))(128–130° C.); $^1H$ NMR (300 MHz, $CDCl_3$): δ 3.93 (12H, s, $OCH_3 \times 4$), 5.82 (1H, s, 1-H), 6.48 (2H, d, 16 Hz), 6.88 (2H, d, J=8 Hz), 7.08 (2H, bs), 7.15 (2H, bd), 7.61 (2H, J=16 Hz); $^{13}CNMR$ (300 MHz, $CDCl_3$): δ 55.9, 56.0, 101.3, 109.8, 111.1, 122.0, 122.6, 128.1, 140.4, 149.2, 151.0, 183.2.

Preparation of pyrazol derivative (8). To a solution of 1–4 in butanol and ethanol were added histidine hydrazide (1 equiv.), acetic acid and p-TsOH. The solution was refluxed for 24 h, and then the solvent was removed in vacuo. The residue was purified by silica gel column chromatography and PLC.

Compound 8. Yellow powder (yield 17.5%), mp 166–168° C. (MeOH); $^1H$ NMR (300 MHz, $CDCl_3$): δ 3.92 (6H, s, $OCH_3 \times 2$), 3.94 (6H, s, $OCH_3 \times 2$), 6.62 (1H, s, 1-H), 6.86 (2H, d, J=8 Hz), 6.93 (2H, d, J=16 Hz), 7.04 (2H, dd, J=8, 2 Hz), 7.06 (2H, bs), 7.05 (2H, d, J=16 Hz); $^{13}CNMR$ (300 MHz, $CDCl_3$): δ 55.8, 55.9, 99.6, 108.6, 111.2, 115.8, 120.1, 129.7, 130.6, 149.1, 149.3; Anal. calcd. for $C_{23}H_{24}N_2O_4 \cdot 1.\frac{1}{4}H_2O$: Theory: C, 66.57; H, 6.44; N, 6.75. Found C, 66.44; H, 6.19; N, 6.27.

Monomethylcurcumin (9). Curcumin (1) in MeOH was treated with excess of diazomethane in $Et_2O$ for 24 h. After removal of solvents, the residue was purified by silica gel column chromatography and PLC to yield a yellow amorphous solid (yield 20%); mp 89–91° C., $[\alpha]_D$ -3.6 (c=1.14, $CHCl_3$); $^1H$ NMR (300 MHz, $CDCl_3$): δ 3.93 (9H, s, $OCH_3 \times 3$), 5.81 (1H, s, 1-H), 5.94 (1H, bs, OH), 6.49 (2H, bd, J=15 Hz), 6.93 (1H, d, J=8 Hz), 6.97 (1H, d, J=8 Hz), 7.10 (4H, m), 7.60 (2H, bd, J=15 Hz); EIMS m/z 382 (M*), HRFABMS 382.1396 $(M+H^+)$ (calcd for $C_{22}H_{22}O_6$: 382.1416).

Hydrogenation of 1, 4 and 10 (11–18). A solution of starting material in EtOAc was shaken with 10% Pd—C under $H_2$ (45 psi) overnight using a Parr's apparatus. The solution was filtered and concentrated in vacuo to give a residue, which was purified by silica gel column chromatography and PLC.

Tetrahydrocurcumin (11). White powder, mp 92–93° C. (Roughley et al., *J. Chem. Soc. Perkin I,* 2379–2388 (1973), 95–96° C.), $^1H$ NMR (300 MHz, $CDCl_3$): δ 2.53–2.58 (3H, m), 2.78–2.88 (5H, m), 3.87 (6H, s, $OCH_3 \times 2$), 5.43 (1H, s, 1-H), 5.50 (2H, s, ArOH), 6.65 (2H, d, J=8 Hz), 6.69 (2H, s), 6.83 (2H, d, J=8 Hz); $^{13}CNMR$ (300 MHz, $CDCl_3$): δ 31.3, 40.4, 55.8, 99.8, 111.0, 114.3, 120.8, 132.6, 144.0, 146.4 and 193.2.

Hexahydrocurcumin (12). White powder, mp 87–88° C. (Roughley, P. J. et al., *J. Chem. Soc. Perkin I,* 2379–2388 (1973), 78–80° C.), $^1H$ NMR (300 MHz, $CDCl_3$): δ 1.60–1.81 (2H, m), 2.53–2.97 (8H, m), 3.85 (6H, s, $OCH_3 \times 2$), 4.06 (1H, m, 2-H), 6.70 (4H, m), 6.80 (2H, d, J=8 Hz); $^{13}CNMR$ (300 MHz, $CDCl_3$): δ 29.7, 31.7, 38.8, 45.8, 49.8, 56.3, 67.4, 111.5, 111.6, 114.8, 114.9, 121.2, 121.4, 133.0, 134.2, 144.2, 144.5, 146.9, 147.9 and 211.9.

Octahydrocurcumin (13). Colorless oil, $^1H$ NMR (300 MHz, $CDCl_3$): δ 1.61 (2H, m), 1.75 (4H, m), 2.53–2.70 (4H, m), 3.80 (6H, s, $OCH_3 \times 2$), 3.91 (2H, brs), 6.13 (2H, s, ArOH), 6.65 (2H, d, J=8 Hz), 6.69 (2H, bs) 6.82 (2H, bd, J=8 Hz), $^{13}CNMR$ (300 MHz, acetone-$d_6$): δ 31.1, 39.8, 42.6, 35.6, 72.0, 111.0, 114.3, 120.6, 133.6, 143.6 and 146.4.

Compound 14. White powder (yield 26.0%), mp 60–61° C., $^1H$ NMR (300 MHz, $CDCl_3$): δ 2.56 (3H, m), 2.86 (5H, m), 3.85 (12H, s, $OCH_3 \times 4$), 5.44 (1H, s, 1-H), 6.71 (4H, m), 6.78 (2H, bd); Anal. calcd. for $C_{23}H_{28}O_6 \cdot \frac{1}{4}H_2O$: Theory: C, 68.21; H, 7.09. Found C, 68.25; H, 7.06.

Compound 15. White powder (yield 20.0%), mp 94–95° C., $^1H$ NMR (300 MHz, $CDCl_3$): δ 1.65–1.80 (2H, m), 2.53–2.84 (8H, m), 3.85 (12H, s, $OCH_3 \times 4$), 4.05 (1H, bs, 2'-H), 6.68–7.23 (4H, m), 6.79 (2H, bd), Anal. calcd. for $C_{23}H_{30}O_6 \cdot \frac{1}{4}H_2O$: Theory: C, 67.88; H, 7.55. Found C, 67.73; H, 7.49.

Compound 16. Colorless oil (yield 4.2%), mp 60–61° C., $^1H$ NMR (300 MHz, $CDCl_3$): δ 1.55–1.65 (4H, m), 1.73–1.82 (3H, m), 2.60–2.72 (3H, m), 3.86 (6H, s, $OCH_3 \times 2$), 3.87 (8H, bs, $OCH_3 \times 2,2,2'$-H), 6.72–6.78 (4H, m), 6.79 (2H, bd), 7.27 (2H, s, $OH \times 2$), EIMS m/z: 404 (M+), HRFAB-MS m/z 404.219070 $(M+H)^+$ (calcd for $C_{23}H_{32}O_6$: 404.2198891).

Compound 17. Colorless oil (yield 5.9%), 1H NMR (300 MHz, $CDCl_3$): δ 1.10 (3H, d), 1.80 (1H, m), 2.43–2.82 (8H, m), 3.86 (6H, s, $OCH_3 \times 2$), 3.87 (6H, s, $OCH_3 \times 2$), 3.94 (1H, bs, 2'-H)*0.70–6.78 (6H, m), EIMS m/z 416 (M+).

Compound 18. Colorless oil (yield 6.95%), $^1H$ NMR (300 MHz, $CDCl_3$): δ 0.95 (3H, d, 1-$CH_3$), 1.52 (1H, m), 1.84 (2H, m), 2.67 (6H, m), 3.83 (14H, bs, $OCH_3 \times 4$, 2, 2'-H), 6.78 (6H, m); EIMS m/z: 418 (M+), HRFAB-MS m/z 418.236618 $(M+H)^+$ (calcd for $C_{24}H_{34}O_6$: 418.2355392).

Preparation of 19 and 20. A mixture of curcumin (1, 100 mg, 0.81 mmol) in acetone (20 mL) with methylchloroacetate (2 mL) and NaI (20 mg) was refluxed with anhydrous potassium carbonate (176 mg) for 24 h with stirring. After filtration and removal of solvent, the residue was purified by silica gel column chromatography to yield the corresponding methyl acetates 19 and 20.

Compound 19: Yellow powder (yield 20.0%), mp 60–61° C., mp 66–67° C., $[\alpha]_D$ -2.4 (c=2.08, $CHCl_3$); $^1H$ NMR (300 MHz, acetone-$d_6$): δ 3.73 (3H, s, —$COOCH_3$), 3.86 (6H, s, $OCH_3 \times 2$), 4.79 (2H, s, O—$CH_2$—COO), 5.99 (1H, s, 1-H), 6.70 and 6.73 (both 1H, d, J=15.3 Hz), 6.88 (1H, d, J=8 Hz), 6.94 (1H, d, J=8 Hz), 7.17 (2H, m), 7.33 (2H, m), 7.59 and 7.61 (both 1H, d, J=15.3 Hz), $^{13}CNMR$ (300 MHz, $CDCl_3$): d 51.8, 55.9, 55.9, 65.9, 101.4, 111.2, 111.6, 114.3, 115.9, 121.8, 122.6, 123.0, 123.5, 127.6, 128.7, 129.8, 140.3, 141.3, 148.4, 149.8, 150.0, 150.4, 169.4, 183.4, 184.6; Anal. calcd. for $C_{24}H_{24}O_8 \cdot \frac{3}{4}H_2O$: Theory: C, 63.50; H, 5.66. Found C, 63.53; H, 5.65.

Compound 20: Yellow powder (yield 20.0%), mp 141–142° C. (MeOH), $[\alpha]_D$ -0.29 (c=5.86, $CHCl_3$); $^1H$ NMR (300 MHz, $CDCl_3$): δ 3.80 (6H, s), 3.93 (6H, s), 4.73 (4H, s, O—$CH_2$—$COO \times 2$), 5.82 (1H, s, 1-H), 6.50 (2H, d, J=16 Hz), 6.79 (2H, d, J=8 Hz), 7.09 (4H, bs), 7.58 (2H, d, J=16 Hz), $^{13}C$ NMR (300 MHz, $CDCl_3$): d 52.3, 56.0, 66.0, 101.4, 110.7, 113.6, 122.0, 122.7, 129.5, 140.1, 149.0, 149.7, 169.0, 183.1; Anal. calcd. for $C_{27}H_{28}O_{10} \cdot \frac{1}{2}H_2O$: Theory: C, 62.18; H, 5.60. Found C, 62.31; H, 5.57.

Compound 21: Yellow amorphous solid (yield 3.0%), $^1H$ NMR (300 MHz, $CDCl_3$): δ 2.58 (2H, m), 2.95 (2H, m), 7.12 (2H, d, J=15 Hz), 7.40 (6H, m), 7.60 (4H, m), 7.81 (2H, d, J=15 Hz), 12.65 (1H, bs); Anal. calcd. for $C_{22}H_{20}O_4$: Theory: C, 75.84, H, 5.79. Found C, 75.56, H, 5.74.

Compound 22: Yellow amorphous solid (yield 25.0%), Anal. calcd. for $C_{26}H_{28}O_8$: Theory: C, 66.66, H, 6.02. Found C, 66.38, H, 6.16.

Compound 23: Yellow powder (yield 45.0%), mp 144–146° C. (MeOH) (Pedersen et al., *Liebigs Ann. Chem.* 1557–1569 (1985), 71–73° C. ($CH_2Cl_2$)) Anal. calcd. for $C_{24}H_{26}O_8 \cdot 2 \cdot \frac{1}{2}H_2O$: Theory: C, 59.87; H, 5.23. Found C, 59.94; H, 5.11.

The structures of 14, 10–13, 22, and 23 were confirmed by comparison of their physical spectral data with those reported in the literature. Pedersen et al., *Liebigs Ann. Chem.* 1557–1569 (1985), Roughley et al., *J. Chem. Soc. Perkin I*, 2379–2388 (1973).

B. Suppression of DHT-Mediated Transcription Activity.

Cell Culture and Transfections. Human prostate cancer DU145 and PC-3 cells were maintained in Dulbecco's minimum essential medium (DMEM) containing penicillin (25 units/mL), streptomycin (25 μg/mL), and 10% fetal calf serum (FCS). For AR transactivation assay, PC-3 cells were transfected with an AR expression plasmid and reporter gene. Because of a low content of endogenous AR coactivators, DU-145 cells were transfected with expression plasmids for AR and ARA70, and reporter gene. The conditions were followed as previously described in Miyamoto et al., *Proc. Natl. Acad. Sci. USA*, 95, 7379–7384 (1998), with minor modifications.

Transfections were performed using the SuperFect kit according to manufacturer's procedures (Qiagen, Chatsworth, Calif.). Briefly, $1 \times 10^5$ cells were plated on 35-mm dishes 24 h before transfection, and then a reporter plasmid, MMTV-Luciferase, which contains MMTV-LTR promoter and AR-binding element, was co-transfected with an AR expression plasmid (wild type or mutant), or pSG5ARA70. PRL-TK was used as an internal control for transfection efficiency. The total amount of DNA was adjusted to 3.0 g with pSG5 in all transcriptional activation assays. After a 2 h transfection, the medium was changed to DMEM-10% charcoal stripped serum medium, and 14–16 h later, the cells were treated with DHT, antiandrogen, or test compounds. After another 14–16 h, the cells were harvested and tested for luciferase activity in luciferase assays (Promega, Dual Luciferase Assay System, Madison, Wis.). Data were expressed in relative luciferase activity as compared to an internal luciferase positive control.

C. Results and Discussion

The aim of this work was to investigate novel curcumin analogues for antiandrogen receptor antagonist activity. The synthesis and evaluation of novel curcumin analogues as antiandrogen receptor antagonists and antitumor agents are reported herein.

Figure 3A:
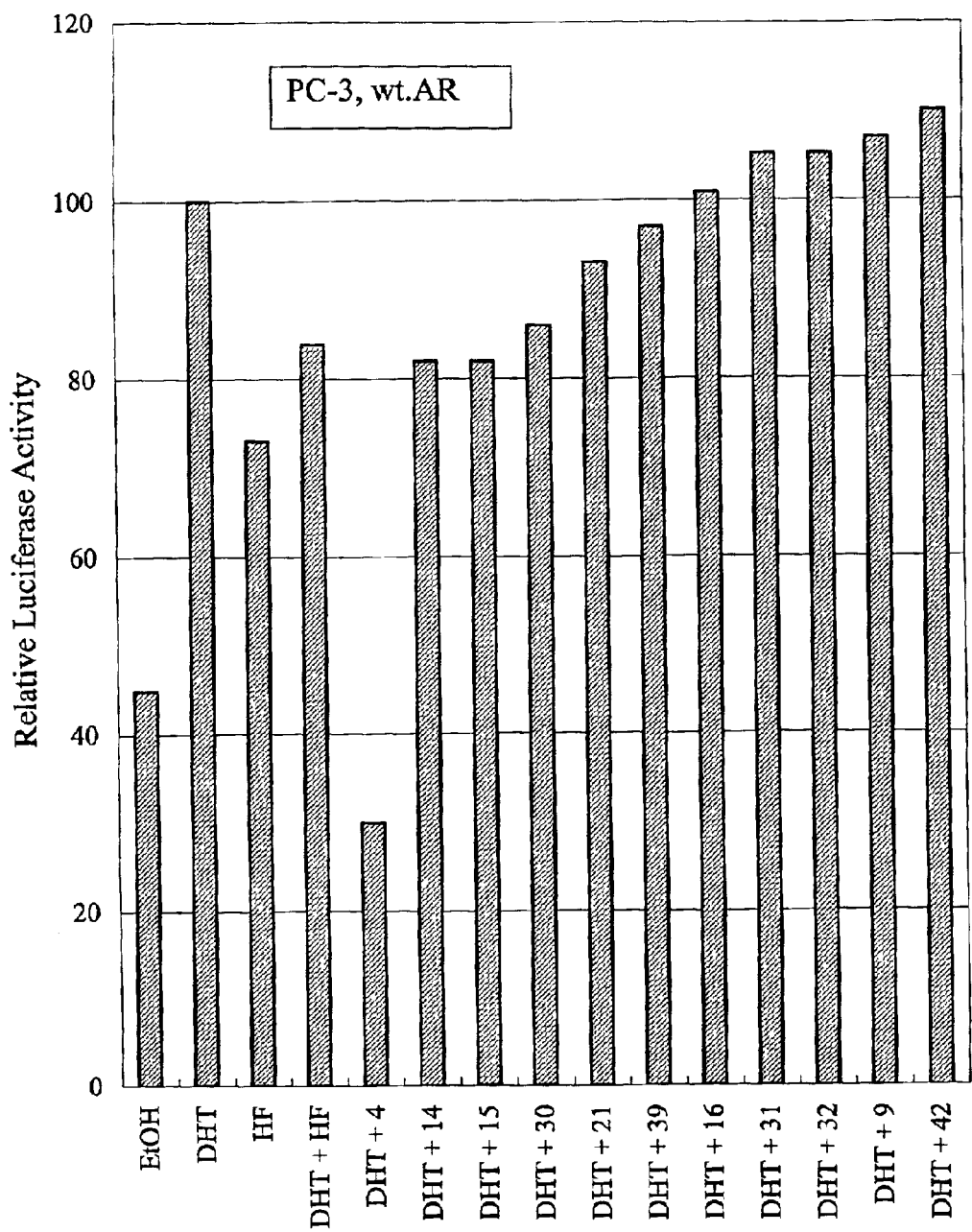
FIG. 3A illustrates suppression of DHT-mediated MMTV transcription AR activity by hydroxyflutamide (HF) and selected compounds.
Figure 3B:
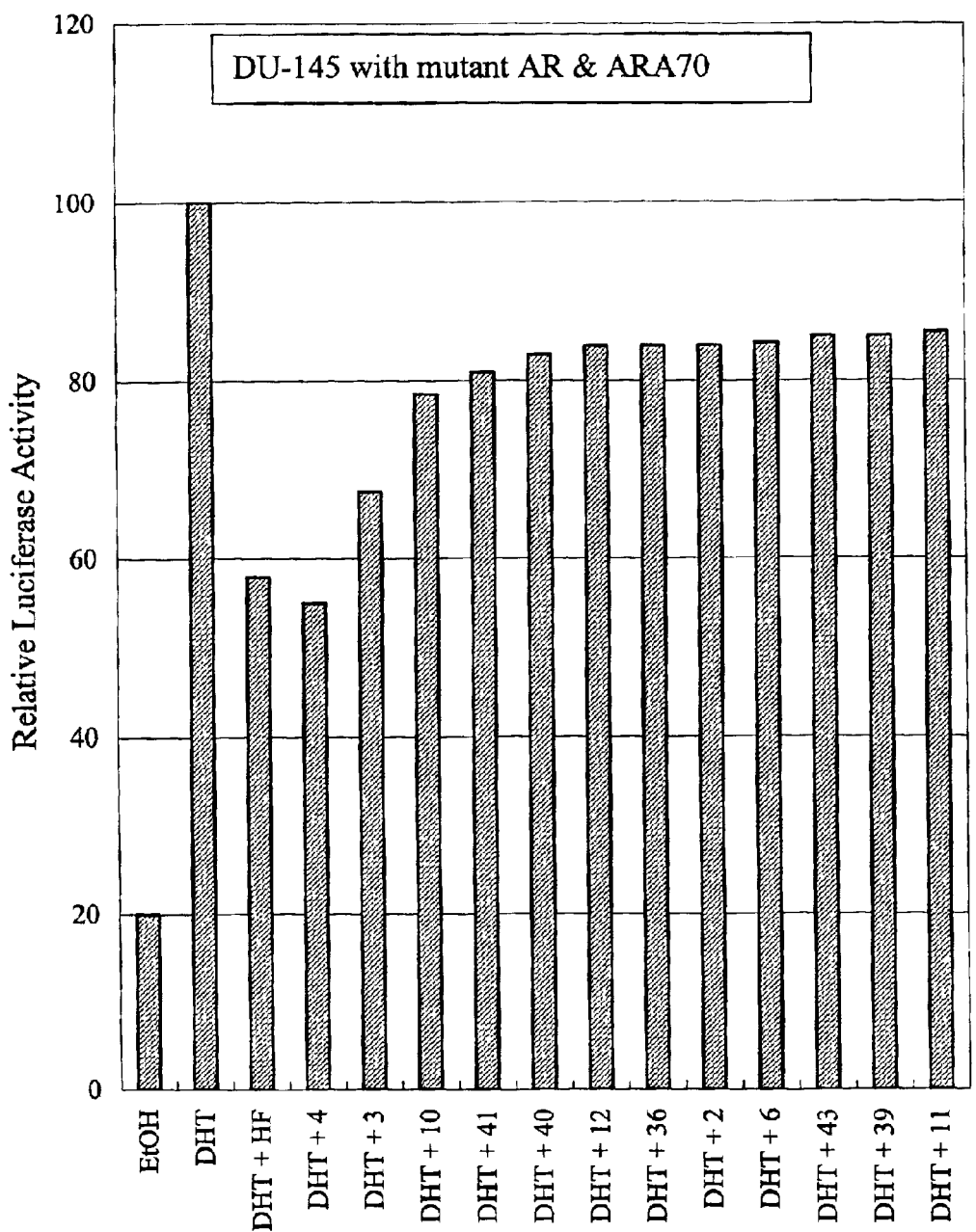
FIG. 3B illustrates suppression of DHT-mediated MMTV transcription AR activity by hydroxyflutamide (HF) and selected compounds.
Figure 3C:
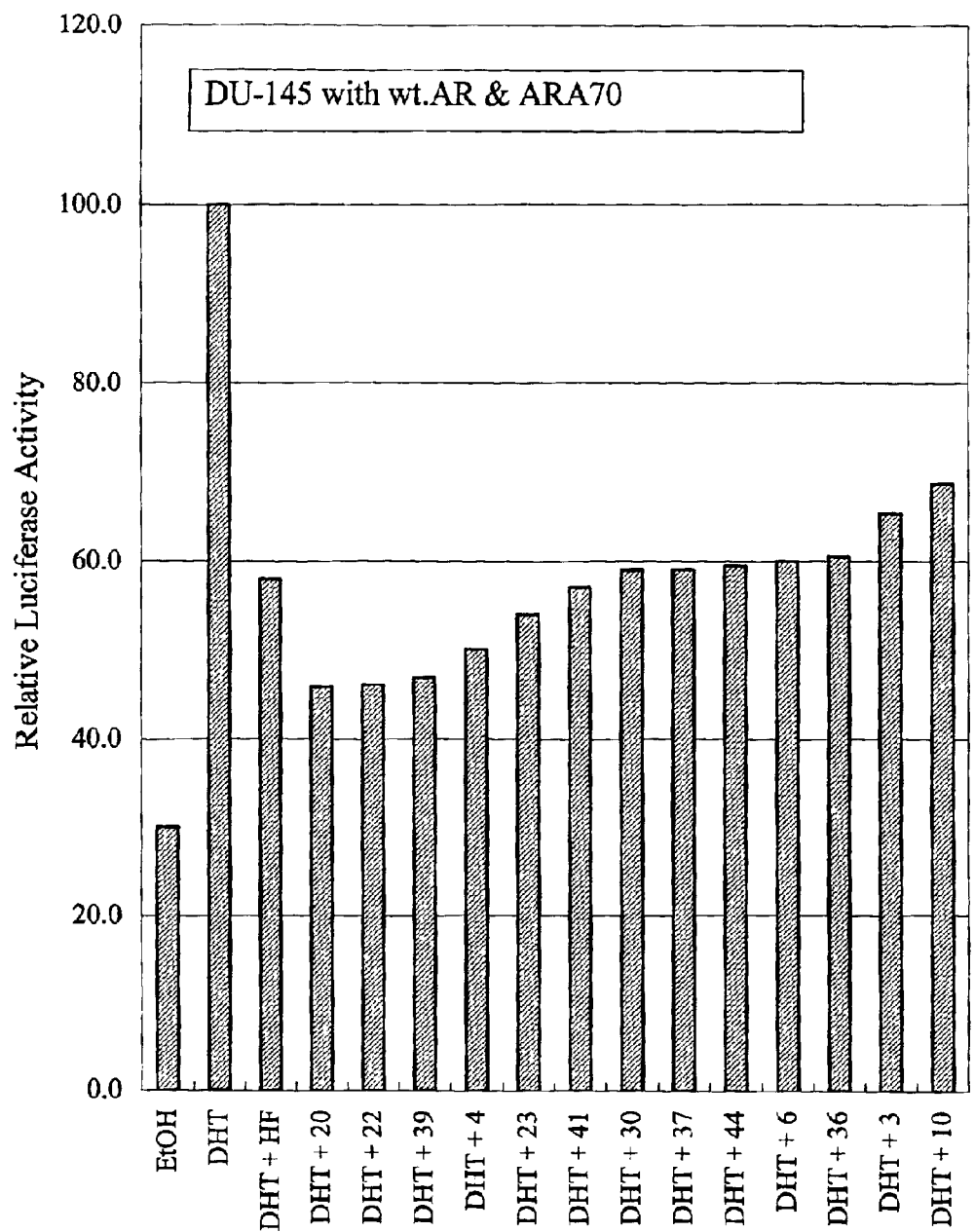
FIG. 3C illustrates suppression of DHT-mediated MMTV transcription AR activity by hydroxyflutamide (HF) and selected compounds.

Forty-seven curcumin derivatives (1–47) were tested for antagonistic activity against the AR using two different human prostate cancer cells, PC-3 and DU-145 (FIGS. 3A–C). The parental compound, curcumin (1), was inactive in all cases. However, dimethylated curcumin (4) showed significant antagonistic activity (reducing 70% of DHT-induced AR activity) when assayed in PC-3 cells transfected with wild-type AR and was more potent than HF (which reduced 16% of DHT-induced AR activity, FIG. 3A). Compound 4 also showed the highest antagonist activity when assayed in DU-145 cells transfected with a mutant LNCaP AR and ARA70 (showing a 45% reduction in DHT-induced AR activity, FIG. 3B), indicating that compound 4 is an effective antagonist for both normal and mutant AR.

To determine the structural requirements for AR antagonist activity in this series of compounds, a structure-activity relationship (SAR) study was conducted in a PC-3 cell assay system. Compared with 4, monomethylated curcumin (9) lacks one O-methyl groups at the p-position on one benzene ring, and was significantly less active than 4 (FIG. 3B). Thus, the bis(3,4-dimethoxyphenyl) groups of 4 are important to the activity. Introducing a methyl group at C-4 of 4 (10) resulted in decreased activity (FIG. 3B). Compounds 14 and 15, which were obtained by hydrogenation of 4, were as potent as HF with an 18% reduction in DHT-induced AR activity, but were considerably less active compared to 4 (FIG. 3A). Converting the β-diketone moiety of 4 to the corresponding pyrazol derivative 8 greatly reduced the activity. Furthermore, 1,3-bis(3,4-dimethoxyphenyl)-1,3-propandione (39), which contains the bis-aryl groups found in 4 but lacks the conjugated double bonds, was less active than 4 (FIGS. 3A and 3B), indicating that the conjugated double bonds also contribute to the activity of 4. These observations suggested that the bis(3,4-dimethoxyphenyl) groups and the conjugated β-diketone moiety are crucial for the activity.

Data in FIG. 3C show a somewhat different cell assay system where antiandrogen activity was assayed in DU-145 cells transfected with wild-type AR and ARA70. Compounds 4, 20, 22, 23, and 39 showed comparable or more potent antiandrogen activity than HF in this assay system. Compounds 20 and 22 were almost equipotent (54% and 53.8% reduction, respectively) and were slightly more active than 4 (49.9%). Because curcumin (1) itself was not active, introducing either methoxycarbonylmethyl groups at the phenolic hydroxyls (20) or an ethoxycarbonylethyl group at C-4 (22) greatly contributed to the anti-AR activity in DU-145 cells in the presence of wild-type AR and ARA70.

In this study, we also examined the antiandrogen activity of fluorodiarylheptanoids 24–29 and cyclic diarylheptanoids 30–38. Compounds 24–29 have fluorine or trifluoromethyl substituents on both benzene rings, but showed weak activity or were inactive. Among the cyclic diarylheptanoids 30–38, compound 30 was the most active and was almost as active as HF (FIGS. 3A and 3C). The remaining cyclic diarylheptanoids showed weak antagonistic activity.

In conclusion, we have prepared a number of curcumin analogues and evaluated their potential antiandrogen activity in three different assay conditions using human prostate cancer cell lines. Compounds 4 showed promising antiandrogen activities in all assays. Compounds 4, 20, 22, 23 and 39 have been identified as a new class of antiandrogen agents. The SAR study revealed that bis(3,4-dimethoxyphenyl) moieties, a conjugated β-diketone, and an ethoxycarbonylethyl group at the C-4 position play important roles in the antagonistic activity.

The foregoing is illustrative of the present invention, and is not to be construed as limiting thereof. The invention is defined by the following claims, with equivalents of the claims to be included therein.

What is claimed is:

1. A compound according to formula I:

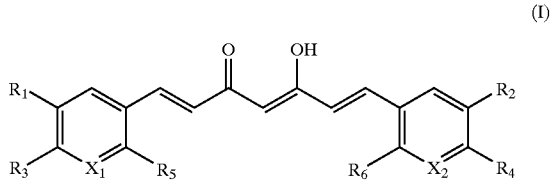

(I)

wherein:
$R_1$ and $R_2$ are each independently selected from the group consisting of alkoxy, nitro, amino, and dialkylamino;
$R_3$ and $R_4$ are each independently selected from the group consisting of hydroxy, alkoxy, and —$OR_7C(O)R_8$, wherein $R_7$ is lower alkylene and $R_8$ is alkoxy;
subject to the proviso that $R_3$ is not hydroxy when $R_1$ is alkoxy, $R_2$ is alkoxy and $R_4$ is hydroxy;
or $R_1$ and $R_3$ together are alkylenedioxy;

or $R_2$ and $R_4$ together are alkylenedioxy;

$R_5$ and $R_6$ are each independently selected from the group consisting of H, halogen, and nitro;

$X_1$ is N, or $X_1$ is C bonded to a H, alkoxy or nitro; and $X_2$ is N, or $X_2$ is C bonded to a H, alkoxy or nitro;

or a pharmaceutically acceptable salt thereof.

2. The compound according to claim 1, wherein $R_1$ and $R_2$ are each independently selected from the group consisting of alkoxy, nitro, amino, and dimethylamino.

3. The compound according to claim 1, wherein $R_1$ and $R_3$ together are methylenedioxy or ethylenedioxy.

4. The compound according to claim 1, wherein $R_2$ and $R_4$ together are methylenedioxy or ethylenedioxy.

5. The compound according to claim 1, wherein $R_5$ and $R_6$ are each independently selected from the group consisting of H, F, and nitro.

6. The compound according to claim 1 having the formula:

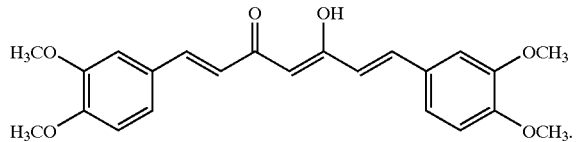

7. The compound according to claim 1 having the formula:

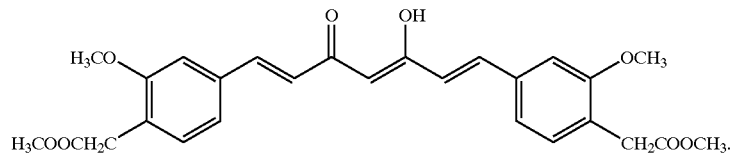

8. A compound according to formula II:

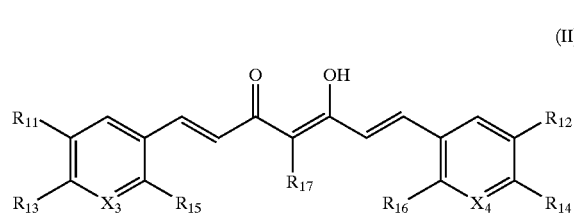

wherein:

$R_{11}$ and $R_{12}$ are each independently selected from the group consisting of alkoxy, nitro, amino, and dialkylamino;

$R_{13}$ and $R_{14}$ are each independently selected from the group consisting of hydroxy, alkoxy, and $-OR_{18}C(O)R_{19}$, wherein $R_{18}$ is lower alkylene and $R_{19}$ is alkoxy;

or $R_{11}$ and $R_{13}$ together are alkylenedioxy;

or $R_{12}$ and $R_{14}$ together are alkylenedioxy;

$R_{15}$ and $R_{16}$ are each independently selected from the group consisting of H, halogen, and nitro;

$R_{17}$ is $-R_{20}C(O)OR_{21}$, wherein $R_{20}$ is alkylene and $R_{21}$ is H or alkyl;

$X_3$ is N, or $X_3$ is C bonded to a H, alkoxy or nitro; and $X_4$ is N, or $X_4$ is C bonded to a H, alkoxy or nitro;

or a pharmaceutically acceptable salt thereof.

9. The compound according to claim 8, wherein $R_{11}$ and $R_{12}$ are each independently selected from the group consisting of alkoxy, nitro, amino, and dimethylamino.

10. The compound according to claim 8, wherein $R_{11}$ and $R_{13}$ together are methylenedioxy or ethylenedioxy.

11. The compound according to claim 8, wherein $R_{12}$ and $R_{14}$ together are methylenedioxy or ethylenedioxy.

12. The compound according to claim 8, wherein $R_{15}$ and $R_{16}$ are each independently selected from the group consisting of H, F, and nitro.

13. The compound according to claim 8 having the formula:

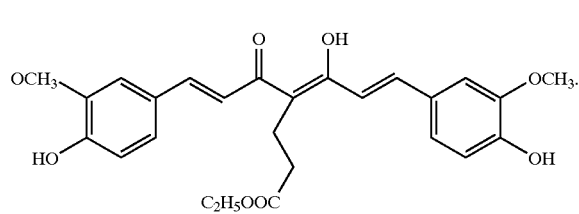

14. The compound according to claim 8 having the formula:

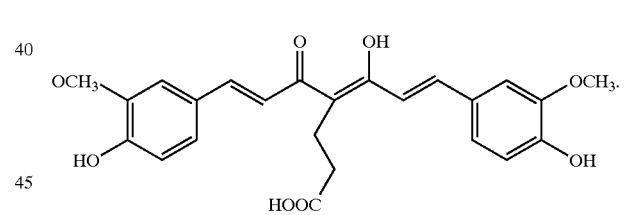

15. A compound according to formula III:

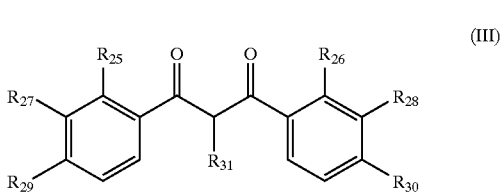

wherein:

$R_{25}$ and $R_{26}$ are each independently H or lower alkyl;

$R_{27}$, $R_{28}$, $R_{29}$ and $R_{30}$ are each alkoxy;

$R_{31}$ is H or lower alkyl;

or a pharmaceutically acceptable salt thereof.

16. The compound according to claim 15 having the formula:

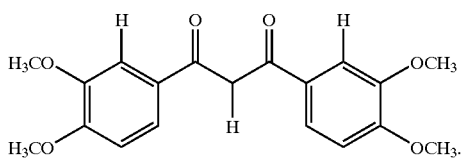

17. A pharmaceutical formulation comprising a compound according to claim 1, 8 or 15 in a pharmaceutically acceptable carrier.

18. The pharmaceutical formulation according to claim 17, wherein said carrier is an aqueous carrier.

19. A method of treating a cancer, comprising administering to a subject in need thereof a treatment effective amount of a compound according to claim 1, 8 or 15.

20. The method according to claim 19, wherein said cancer is selected from the group consisting of skin cancer, small cell lung cancer, testicular cancer, lymphoma, leukemia, esophageal cancer, stomach cancer, colon cancer, breast cancer, endometrial cancer, ovarian cancer, central nervous system cancer, liver cancer and prostate cancer.

21. The method according to claim 20, wherein said cancer is prostate cancer.

22. The method according to claim 20, wherein said cancer is colon cancer.

23. The method according to claim 19, wherein said subject is afflicted with antiandrogen withdrawal syndrome.

24. A method of inducing androgen receptor antagonist activity, said method comprising contacting a cell with an androgen receptor antagonist effective amount of a compound according to claim 1, 8 or 15.

25. The method according to claim 24, wherein said cell is a cancer cell.

26. The method according to claim 24, wherein said contacting step is carried out in vivo.

27. The method according to claim 24, wherein said contacting step is carried out in vitro.

28. A method of inducing androgen receptor antagonist activity in a subject afflicted with an androgen-related affliction, said method comprising administering an androgen receptor antagonist effective amount of a compound according to claim 1, 8 or 15.

29. The method according to claim 28, wherein said subject is afflicted with baldness.

30. The method according to claim 28, wherein said subject is afflicted with hirsutism.

31. The method according to claim 28, wherein said subject is afflicted with a behavioral disorder.

32. The method according to claim 28, wherein said subject is afflicted with acne.

33. The method according to claim 27, wherein said subject is a male subject and said androgen receptor antagonist effective amount of a compound according to claim 1, 8 or 15 inhibits spermatogenesis.

* * * * *